United States Patent [19]

Verbeck

[11] 3,993,451

[45] *Nov. 23, 1976

[54] TEST FOR A GIVEN CONSTITUENT IN A LIQUID

[75] Inventor: Bruno J. Verbeck, San Diego, Calif.

[73] Assignee: Miles Laboratories, Inc., Elkhart, Ind.

[ * ] Notice: The portion of the term of this patent subsequent to June 27, 1989, has been disclaimed.

[22] Filed: Nov. 8, 1974

[21] Appl. No.: 521,971

Related U.S. Application Data

[63] Continuation of Ser. No. 265,645, June 23, 1972, Pat. No. 3,847,553, which is a continuation-in-part of Ser. No. 64,090, July 24, 1970, Pat. No. 3,672,845, which is a continuation of Ser. No. 703,002, Feb. 5, 1968, abandoned.

[52] U.S. Cl. .............................. 23/253 TP; 195/127
[51] Int. Cl.² .................. C12K 1/10; G01N 31/22; G01N 33/16
[58] Field of Search ................ 23/253 TP, 230 B; 195/95, 103.5 R, 103.5 C, 127

[56] References Cited
UNITED STATES PATENTS

| | | |
|---|---|---|
| 2,249,867 | 7/1941 | Snelling ....................... 23/253 TP X |
| 2,785,057 | 3/1957 | Schwab et al. ................... 23/253 TP |
| 2,918,893 | 12/1959 | Norton ..................... 23/253 TP UX |
| 3,002,385 | 10/1961 | Wahl et al. ................ 23/253 TP UX |
| 3,018,611 | 1/1962 | Biritz .......................... 23/253 TP X |
| 3,092,465 | 6/1963 | Adams, Jr. et al. .............. 23/253 TP |
| 3,311,084 | 3/1967 | Edenbaum ............... 23/253 TP UX |
| 3,552,925 | 1/1971 | Fetter ............................. 23/253 TP |
| 3,847,553 | 11/1974 | Verbeck .......................... 23/253 TP |

Primary Examiner—Joseph Scovronek
Attorney, Agent, or Firm—Bruno J. Verbeck

[57] ABSTRACT

The device, for use in analysis of a sample of liquid material applied thereto, comprises a plastic film support having adhered to one surface thereof a reagent-containing layer, said reagent reacting with a component of said sample to produce a color change within said layer, said layer also containing reagent-free particles of hydrophilic, absorbent, porous, particulate material, adhered to said surface, and on the opposite side of said reagent-containing layer from said support, a layer of a porous medium through which some of the said component is transmitted to said reagent-containing layer.

2 Claims, 5 Drawing Figures

TEST FOR A GIVEN CONSTITUENT IN A LIQUID

This is a continuation of applicant's Ser. No. 265,645, filed June 23, 1972, now U.S. Pat. No. 3,847,553 issued Nov. 12, 1974; the latter was a continuation-in-part of applicant's Ser. No. 64,090, filed July 24, 1970, now U.S. Pat. No. 3,672,845, issued June 27, 1972; the latter was a streamline continuation of applicant's Ser. No. 703,002, filed Feb. 5, 1968, now abandoned.

DESCRIPTION OF THE INVENTION

This invention is concerned with new and useful testing devices for determining and detecting the presence of a constituent of a liquid.

Test devices for the detection of the presence of a constituent of a liquid, in the form of paper strips which have been dipped in a solution of various chemicals and then dried, are widely used because they have made it possible to detect constituents in liquids in a simple, convenient way without the necessity of using laboratory equipment, liquid reagents, test tubes, Bunsen burners and the like, or technical personnel skilled in carrying out conventional types of tests such as clinical tests. The aforesaid test devices represent an important contribution to the art and science of diagnosis.

The present invention has as one object the provision of improved testing devices for the determination and detection of a constituent of a liquid.

A further object is the provision of a new and useful testing device, for the detection of a constituent of a liquid, having improved performance characteristics.

A further object is the provision of a new and useful testing means, having improved reproducibility characteristics, for the detection of a constituent of a liquid, which does not require skilled personnel, liquid reagents, heat, test tubes and the like.

Still another object is the provision of an improved testing device for the determination of and detection of a component in a body fluid, such as urine, blood, serum and the like.

The present invention encompasses a multi-layer testing device for use in analysis of a sample of liquid material applied thereto, comprising a plastic film support having adhered to one surface thereof a reagent-containing layer, the said reagent reacting with a component of said sample to produce a color change within the said layer, that layer also containing reagent-free particles of hydrophilic, particulate material adhered to said surface, and on the opposite side of said reagent-containing layer from said support, a layer of a porous medium through which some of the said component is transmitted to said reagent-containing layer.

The present invention also encompasses an indicator device for determining a constituent of a liquid which device comprises (1) a dry hydrophilic absorbent material which incorporates indicator material remaining from impregnation of said absorbent material with a solution of said indicator, followed by drying, and (2) a dry hydrophilic absorbent material which incorporates a composition, which reacts with the said constituent to form a reaction product, which reacts with and causes said indicator to change color, said composition having been deposited in said absorbent material by means of an impregnation of it with a solution of said composition, followed by drying.

The two thus-treated dry hydrophilic absorbent materials together are formed into a single integral testing unit which, in use, is contacted with a specimen of the liquid being tested and the color change, if any, observed to determine the presence or absence of the constituent being tested for, in that liquid.

It is, thus, in one embodiment, a feature of this invention that the impregnating solutions be, each of them, incorporated in separate portions of hydrophilic absorbent particulate material. In one embodiment of a test device the hydrophilic absorbent, particulate material is composed of a dry mixture of (a) particles which have been impregnated with a solution of the indicator and then dried, and (b) particles which have been impregnated with a solution of a composition which reacts with the constituent in the liquid to be tested, to form a reaction product which reacts with said indicator to effect a color change therein.

Hydrophilic, absorbent, particulate material which may be used in the practice of my invention includes silica gel, aluminum oxide, powdered cellulose, exfoliated vermiculite and the like.

The mixture of the solution impregnated particulate material may be secured with an adhesive and/or pressure to one or more surfaces of a carrier which may itself be hydrophilic absorbent material such as paper in sheet form, or it may be in the form of a hydrophobic or hydrophilic non-absorbent sheet material. Dry particulate material such as silica gel, aluminum oxide, powdered cellulose, exfoliated vermiculite, or the like, may be added, per se, to the mixture of the dried, solution impregnated particles. If such particulate material is added, it is desirable that it have incorporated therein a wetting agent preferably dried after such incorporation, so that those dry particles would be, preferentially, more readily wetted by the liquid with which the whole indicator device is subsequently contacted.

Typical of suitable wetting agents are, for example, Aerosol OT Di(2-ethylhexyl) ester of sodium sulfo-succinic acid; Tween 20 Tris (polyoxyethylene) sorbitan monolaurate; and Tween 80 Tris(polyoxyethylene) sorbitan monooleate.

The dry indicator-impregnated component, and the component impregnated with the composition which is reactable with the constituent in the liquid being determined, with or without added cellulose powder, aluminum oxide, silica gel, exfoliated vermiculite or other particulate material, may be compacted, as in a pill-forming machine to form compressed, frangible structures, which may be secured to a carrier, such as a strip of paper, plastic or the like, by any suitable means, and the test carried out by dipping the resulting device into the liquid being tested and observing the appearance or non-appearance of a color change. Or, the compressed, frangible structure may be fractured and particulated to a limited extent to form irregularly shaped agglomerates of the component particles, having essentially the same composition as the un-fractured, which agglomerates are then applied suitably by means of adhesive to a carrier strip such as above described. It is a particular advantage of this form of the invention that the test is carried out more rapidly and more effectively since the irregular surface character of such agglomerates provides substantially more surface area and results in more rapid wetting and quicker achievement of the test.

The invention is applicable to the provision of tests for determining the presence in various liquids of constituents of such liquids. Thus the test devices can be so constructed as to be able to determine the presence of a constituent in body fluids such as blood, urine and the like. The reagents used in the fabrication of my devices are those which are well known and previously used in diagnostic tests. Albumin, for example, is detected by use of an indicator dye which exhibits protein error, and a buffer composition for maintaining the pH of the liquid with which the test device is to be contacted at a predetermined pH; glucose in urine can be determined by use of glucose oxidase, peroxidase and an indicator whose color is affected by hydrogen peroxide in the presence of peroxidase; urea can be detected with urease and a dye which is color responsive to changes in pH.

The invention will be further illustrated by reference to the accompanying drawings of an illustrative embodiment, one for determining and detecting the presence of albumin in urine, in which:

FIG. 1 is a view of an embodiment showing a sheet material having attached to one surface thereof absorbent particles containing thereon, or therewithin, an indicator dye which exhibits protein error, and particles containing thereon, or therewithin, a buffer composition for maintaining the pH of the urine with which said embodiment is to be contacted, at a predetermined pH.

FIG. 2 shows an embodiment of my invention wherein a carrier has attached to at least one surface thereof a layer or coating of absorbent particles containing thereon or therewithin an indicator dye which exhibits protein error, the same coated surface being in physical contact with a second carrier having attached thereto a layer of absorbent particles which have been treated with, and contain therein, or thereon, a buffer. The two thus-coated carriers are then attached to each other as by treating one or both coated surfaces with an adhesive followed by pressing the coated faces together.

Figure 5:

FIG. 5 shows another embodiment of my invention wherein a carrier has secured to it agglomerates, which agglomerates comprise a mixture of particulate material which has been impregnated with a solution of an indicator component which exhibits protein error, and then dried, in admixture with particulate material which has been impregnated with a buffer material and then dried, which mixture has been compacted to form a compressed frangible structure, and the resulting structure then particulated to form the said agglomerates.

Figure 1:
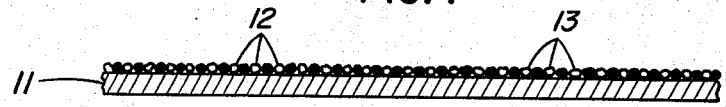

Referring further to FIG. 1, the device there shown comprises a sheet 11 of material, which is suitably an absorbent hydrophilic paper which has adhesively secured to at least one surface thereof, a uniform continuous layer of homogeneous mixture of particles 12 and 13. Particles 12 can be, for example, powdered cellulose, alumina, silica gel, exfoliated vermiculite or the like, which material has been treated with one of the indicators such as described above, which exhibits the phenomenon known in the art as protein error, which indicator material can be applied into, or onto, the particulate material by impregnating the particulate material with a solution of the dye, followed by drying.

Particles 13 comprise particulate material such as powdered cellulose, alumina, silica gel, exfoliated vermiculite, or the like, which material has been impregnated with a solution of buffer material, which may consist of a salt as described above, or mixtures thereof, for the purpose of buffering the urine which comes in contact therewith within or below the range through which the indicator used in preparing particles 12 changes color due to a change in pH. This buffer-containing material is likewise dried after preparation.

The dry indicator-impregnated particles 12 and the dry buffer-impregnated particles 13 are mixed to form a homogeneous mixture and the resulting mixture of particles then adhesively secured to sheet 11 by means of any suitable adhesive, of which pressure-sensitive adhesives are typical. A suitable adhesive is a butadiene-styrene rubber-based adhesive having a high solids content in relation to the solvent content. Such butadiene-styrene rubber-based adhesive lends itself to application in the form of a spray from an aerosol container without unduly misting or becoming stringy during application. An example of a presently commercially available product is that marketed by Minnesota Mining and Manufacturing Corporation of St. Paul, Minn., and identified as "Adhesive Spray No. 77".

Figure 2:
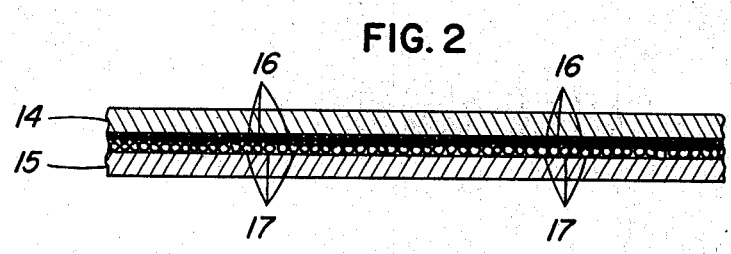

With further reference to FIG. 2, it shows a test device comprising sheets 14 and 15, suitably of hydrophilic, absorbent material such as paper, each of which has adhesively secured thereto a uniform, continuous layer of particulate material. Particles 16 may be either powdered cellulose, aluminum oxide, silica gel, exfoliated vermiculite, or a mixture thereof, which has been impregnated with one of the indicator dyes previously described which exhibits protein error, followed by drying, and which is adhesively secured to sheet 15. Particulate material 17 comprises cellulose powder, alumina, silica gel, exfoliated vermiculite, or a mixture thereof, which has been impregnated or otherwise treated with a solution of buffer salt or an acid such as described above, and then dried to maintain the pH of the urine, with which the device will come in contact during testing, at a pH which is within or below the range through which the indicator changes color as a result of changes in pH.

Figure 3:
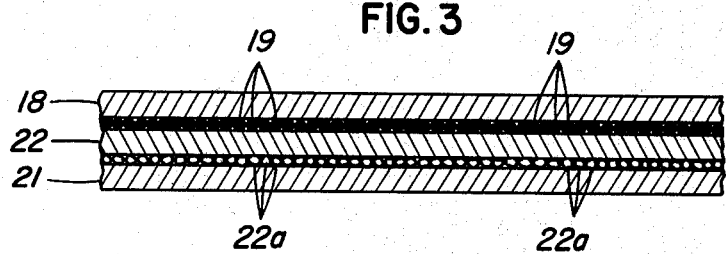
FIG. 3 shows a form of my invention generally similar to that shown in FIG. 2, but having additionally positioned as shown, an absorbent hydrophilic sheet material between, and separating, the two outer sheets, one of which has on it particulate materials which have been treated with dye, and the other a buffer, the whole forming an integral unit.

Further referring to FIG. 3, it shows another embodiment of my invention wherein a sheet 18 of material, which may be hydrophilic absorbent paper, such as rice paper, has adhesively secured to it a layer comprising particulate material 19 such as cellulose, alumina, silica gel, exfoliated vermiculite, or a mixture thereof, which has been impregnated or otherwise treated with a solution of an indicator material which undergoes protein error and then dried. A second sheet 21 which may be identical with sheet 18 has adhesively secured to it a layer of particulate material 22a of powdered cellulose, alumina, silica gel, exfoliated vermiculite, or a mixture thereof, which particulate material has been impregnated with a solution of buffer salt or an acid and then dried. Adhesively securing the two thus-coated sheets 18 and 21 together, is a sheet 22 of a preferably hydrophilic, absorbent material such as rice paper, the adhesive being selected, for example, from any of the numerous well-known pressure sensitive adhesives used in the manufacture of pressure sensitive tapes, and the like. It is preferably treated with a wetting agent, and dried if necessary, to make it more hydrophilic.

Figure 4:
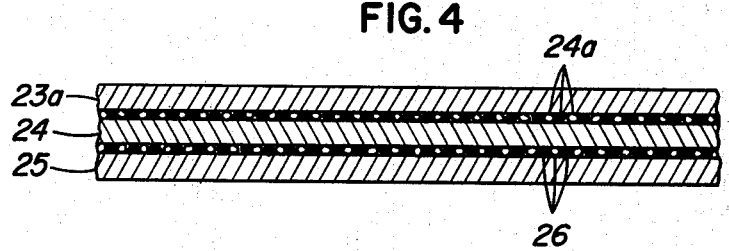
FIG. 4 shows another embodiment of my invention similar to that shown in FIG. 3 except that the particulate coating contains, in addition, absorbent particulate material which does not contain added reactants.

The embodiment in FIG. 4 illustrates a laminate formed of superimposed sheets of hydrophilic absorbent material wherein sheet 23a is a hydrophilic, absorbent material, such as filter paper or rice paper, and 24 is a sheet of hydrophilic, absorbent material, also a paper, containing a layer of particulate material 24a, the layer being formed of a mixture of particles, such as cellulose powder, one part of the mixture being untreated while the remaining part has been impregnated with a solution of a buffer salt, dried, and after mixing with the untreated portion, adhesively secured to sheet 24. Sheet 25 is likewise a hydrophilic, absorbent sheet material which has been coated with a layer of particulate material 26 this being a mixture of particles, such as cellulose powder, one part of the mixture being untreated, while the remaining part has been impregnated with a solution of an indicator material which exhibits protein error, dried, mixed with the untreated powder, and the mixture then coated onto sheet 25. The sheets 23, 24 and 25 are laminated together by the use of adhesives; only sufficient adhesive is used to secure the laminates one to the other, as by spotting, without substantially interfering with the hydrophilic, absorptive character of the laminate so that when a sample of urine to be tested is applied to the top or bottom layer of the laminate, or if the laminate is immersed in a sample of urine, there will be permeation of the liquid through the components of the laminate.

The buffer and indicator in the foregoing embodiments can be applied to the particulate absorbent material in the form of a spray, as by application from an aerosol can containing the buffer composition or the indicator composition, it being understood of course that the particulate, absorbent material containing the buffer components, and the particulate, absorbent material containing the indicator compound be dried before being placed in proximity to each other.

With further reference to FIG. 5, the device there shown comprises a sheet 28 of a material which may be either an absorbent hydrophilic material, such as paper, or may be water-insoluble plastic material. Adhesively secured to at least one surface of sheet 28 is a uniform, continuous layer of agglomerates 29. These agglomerates may be of any suitable size, conveniently from about 10 mesh to 50 mesh, although the particle size is not precisely critical. These agglomerates have been prepared by pressing the dried mixture of particles such as those described in connection with FIG. 1, and the resulting compressed frangible structure particulated to form the agglomerates. These are adhesively secured to the surface of the carrier conveniently by the use of a suitable adhesive. An additional sheet 28a may be superimposed over the agglomerates shown in FIG. 5 so as to have them sandwiched between two sheets, at least one of which is preferably a hydrophilic, absorbent material such as paper.

For purposes of illustration, the following specific examples will describe the invention in greater detail, it being understood that variations within the scope of the invention will occur to those skilled in the art.

EXAMPLE I 15 g. of a 2:1 mixture of anhydrous citric acid and sodium citrate dihydrate is dissolved in 100 ml. water. This solution is then added to 10 g. of finely divided chemically purified wood cellulose particles (alpha-cellulose) which vary typically from about 15–25 microns in diameter and 35–165 microns in average length, thoroughly mixed and when the particles have been thoroughly wetted, excess liquid is removed, and the thus impregnated, finely divided particles dried at 100° C.

Another solution is made up consisting of 0.005 g. Tetrabromphenol blue dissolved in 100 ml. of water, and 10 g. chemically purified wood cellulose particles, as described above, are mixed with the aqueous solution of the dye until thoroughly wetted, excess liquid removed and the thus-treated cellulose is then dried at 100° C.

The dry buffer-impregnated particles are then thoroughly mixed with the dry Tetrabromphenol blue-impregnated particles.

A sheet of Eaton and Dikeman Filter Paper No. 615 is lightly coated with an adhesive by spraying it with Adhesive Spray No. 77, previously described, and the two portions of dry impregnated cellulose particles, after thorough mixing, are applied thereover to form a uniform coating or layer.

When dipped momentarily into a specimen of urine containing 0.5% albumin and then withdrawn, the aforesaid test strip turns bluish-green to blue. In the absence of albumin it remains yellow.

EXAMPLE II

The procedure of Example I was followed, except that to the mixture of the two dried batches of cellulose powder, one of which had been impregnated with an aqueous solution of the buffer, and one with dye, there was added in dry form an alpha-cellulose powder equal in weight to one of the batches of treated cellulose. The resulting mixture was then applied to a paper carrier as in Example I. When the resulting device is contacted with a urine specimen containing 0.5% albumin and then withdrawn, it quickly turns bluish-green in color.

EXAMPLE III

The procedure of Example II was followed, except that after the two batches of treated wood cellulose powders were prepared, the buffer-impregnated dry powder was applied to one face of a strip of Eaton and Dikeman Filter Paper No. 615 which had been first treated with sprayed-on adhesive as in Example I. The indicator-impregnated batch of cellulose powder was applied in a similar manner to a second sheet of adhesive-treated paper. The two sheets were then adhesively secured together with the coated sides being in face-to-face relationship.

EXAMPLE IV

The procedure of Example III was followed, except that after the two sheets were prepared, a separator sheet of rice paper was placed therebetween and secured thereto with the spray-on adhesive as in Example I to form an integral unitary test device.

EXAMPLE V

A test device was prepared as follows. The buffer solution described in Example I was impregnated into a sheet of Eaton and Dikeman Filter Paper No. 615 which was then dried at 100° C. A second sheet of similar filter paper was immersed in the indicator solution of Example I and it, too, dried at 100° C. A laminate was then prepared by adhesively securing, using Spray-on Adhesive 77 in face-to-face relationship to each other, as a first layer a sheet of rice paper, a second inner layer of the buffer-impregnated paper, a third, or inner, layer of unimpregnated filter paper, a fourth layer of the indicator-impregnated paper, and a fifth, or outer, layer of rice paper.

By the term "ultimate basic color", as used in this application, I mean that color which manifests itself when further increases in pH do not further intensify the depth of that color. For example, in the case of Tetrabromphenol blue, which undergoes a color change through the range of pure yellow to pure blue when going from a pH of 3.0 to 4.6, the ultimate basic color is manifested at pH 4.6.

While the foregoing description has been directed to the formation of "a layer" of particulate, hydrophilic, absorptive material, it is to be understood, of course, that such layer may be a composite of coatings or layers built up successively to any desired thickness.

The invention is also applicable to the production of improved test systems which contain either an enzyme or an enzyme substrate — depending on whether the one or the other is to be detected in the liquid being tested — as one of the components, as well as an indicator which changes color as a result of reaction between enzyme and substrate. In the production of a test device comprising an indicator and an enzyme, for detecting the presence or absence of the enzyme substrate in a liquid, one portion of particulate hydrophilic absorbent material such as above described, is impregnated with a solution of the enzyme and then dried. A second portion of particulate hydrophilic absorptive material is impregnated with a solution of indicator which is responsive, as by a color change, to the presence of a reaction product formed when the enzyme and its substrate react, and is then dried. The separately dried portions are then mixed together and applied to a carrier such as a plastic film or the like.

Additional portions of absorptive material may be impregnated, each of them, with such additional materials as may be useful in improving the performance characteristics of the test, including buffers, stabilizers and the like, as those skilled in the art will appreciate.

If it is the enzyme — rather than the substrate — whose presence or absence is to be detected in a liquid being tested, then the test device is made up by impregnating one portion of particulate hydrophilic absorptive material with a solution of the substrate for that enzyme, followed by drying, and impregnating a second portion of absorptive material with an indicator which is responsive to a reaction product or products produced as a result of reaction between the enzyme and its substrate. The color changes resulting therefrom include broadly such phenomena as fluorescence and luminescence, depending on the particular enzyme — or substrate — being tested, and the indicator used, as those skilled in the art will understand.

The test devices of the invention are, thus, suitable for detection of such constituents of body fluids as urea, uric acid, phosphatase, including alkaline phosphatase, galactose, and the like, as those skilled in the art will readily appreciate, since diagnostic compositions and preparations for detecting enzyme substrates in which, e.g., bibulous strips of material, such as paper, are impregnated with solutions containing the enzyme of choice plus indicator and dried, are well known. See for example, the test for glucose referred to in U.S. Pat. No. 2,850,359.

Thus, in accordance with the present invention, if, for example, a glucose test device based on the present invention is desired, separate portions of hydrophilic absorptive particulate material as above described, are impregnated with, respectively, a solution of glucose oxidase, a solution of peroxidase and a solution of indicator, followed by drying, the thus impregnated portions of dried impregnated particles mixed together, and then applied onto a carrier such as a plastic film, or compacted and used in the form of a wafer or tablet, or the like, or further particulated and applied to a carrier in such form.

The following example illustrates preparation of a typical test device in accordance with the invention, utilizing an enzyme as a component.

EXAMPLE VI

A solution was made up containing 40 grams of o-tolidine, 1600 ml of 95% ethyl alcohol and 1200 ml of distilled water, and the pH adjusted to 4.6.

This was thoroughly mixed with 300g of finely divided chemically purified wood cellulose particles as further described in Example I, and when the particles were thoroughly wetted the excess liquid was removed and the particles dried at 100° C.

Another solution was made up by dissolving 34 grams of glucose oxidase in 1000 ml of distilled water. This was added to 100 grams of the same type of finely divided cellulose as was used in Example I, mixed, excess liquid removed and the particles air dried.

Still another solution was made up by dissolving 0.34 g. horseradish peroxidase in 1000 ml distilled water, and then added to 100 grams of finely divided cellulose as described above, excess liquid removed and the particles air dried.

Equal amounts by weight of the above three portions of impregnated and dried particles were mixed together, and then applied to a sheet of Eaton and Dikeman Filter Paper No. 615, as described in Example I above. When strips of such treated paper are dipped momentarily into urine which contains pathologically significant amounts of glucose, the test strip turns blue.

It is to be understood that the foregoing description and the examples have been given only by way of illustration, and that the test device of the invention are susceptible of variations without departing from the scope of the invention, which is limited only by the claims which follow.

What is claimed is:

1. A multi-layer testing device for use in analysis of a sample of liquid material applied thereto, comprising a plastic film support having adhered to one surface thereof a reagent-containing layer, said reagent reacting with a component of said sample to produce a color change within said layer, said layer also containing reagent-free particles of hydrophilic, particulate material adhered to said surface, and on the opposite side of said reagent-containing layer from said support, a layer of a porous medium through which some of the said component is transmitted to said reagent-containing layer.

2. The device of claim 1 wherein said reagent-free particles of hydrophilic, particulate material comprise a member selected from the group consisting of aluminum oxide, silica gel, powdered cellulose and exfoliated vermiculite.

* * * * *